(12) United States Patent
Moaddeb et al.

(10) Patent No.: US 7,402,134 B2
(45) Date of Patent: Jul. 22, 2008

(54) MAGNETIC DEVICES AND METHODS FOR RESHAPING HEART ANATOMY

(75) Inventors: Shahram Moaddeb, Irvine, CA (US); Samuel M. Shaolian, Newport Beach, CA (US); Emanuel Shaoulian, Newport Beach, CA (US); Richard Rhee, Anaheim, CA (US); Steven C. Anderson, Rancho Santa Margarita, CA (US)

(73) Assignee: MiCardia Corporation, Irvine, CA (US)

( * ) Notice: Subject to any disclaimer, the term of this patent is extended or adjusted under 35 U.S.C. 154(b) by 0 days.

(21) Appl. No.: 11/142,127

(22) Filed: May 31, 2005

(65) Prior Publication Data

US 2006/0015003 A1 Jan. 19, 2006

Related U.S. Application Data

(60) Provisional application No. 60/588,254, filed on Jul. 15, 2004.

(51) Int. Cl.
*A61F 2/00* (2006.01)
(52) U.S. Cl. ........................................................ 600/37
(58) Field of Classification Search ............... 600/9–15, 600/37; 128/897–899
See application file for complete search history.

(56) References Cited

U.S. PATENT DOCUMENTS

| 5,176,618 | A | 1/1993 | Freedman |
| 5,906,573 | A | 5/1999 | Aretz ............................ 600/3 |
| 5,979,456 | A | 11/1999 | Magovern |
| 6,123,724 | A | 9/2000 | Denker |
| 6,160,084 | A | 12/2000 | Langer et al. |
| 6,165,122 | A | 12/2000 | Alferness |
| 6,174,279 | B1 | 1/2001 | Girard |
| 6,193,648 | B1 | 2/2001 | Krueger |
| 6,332,863 | B1 | 12/2001 | Schweich, Jr. et al. |
| 6,332,864 | B1 | 12/2001 | Schweich, Jr. et al. |

(Continued)

OTHER PUBLICATIONS

Calo-MER™, Shape-Memory Thermoplastic [online], Apr. 8, 2003 [retrieved on May 18, 2005]. Retrieved from the Internet: <URL: http://www.polymertech.com/materials/calomer.html>, 4 pages.

(Continued)

*Primary Examiner*—Samuel G Gilbert
(74) *Attorney, Agent, or Firm*—Aaron D. Barker; Stoel Rives LLP

(57) ABSTRACT

Systems, methods and devices are provided for treating heart failure patients suffering from various levels of heart dilation. Heart dilation treated by reshaping the heart anatomy with the use of magnetic forces. Such reshaping changes the geometry of portions of the heart, particularly the right or left ventricles, to increase contractibility of the ventricles thereby increasing the stroke volume which in turn increases the cardiac output of the heart. The magnetic forces are applied with the use of one or more magnetic elements which are implanted within the heart tissue or attached externally and/or internally to a surface of the heart. The various charges of the magnetic forces interact causing the associated heart tissue areas to readjust position, such as to decrease the width of the ventricles. Such repositioning is maintained over time by the force of the magnetic elements, allowing the damaging effects of heart dilation to slow in progression or reverse.

7 Claims, 15 Drawing Sheets

U.S. PATENT DOCUMENTS

| | | | |
|---|---|---|---|
| 6,388,043 | B1 | 5/2002 | Langer et al. |
| 6,402,679 | B1 | 6/2002 | Mortier et al. |
| 6,416,459 | B1 | 7/2002 | Haindl |
| 6,540,666 | B1 | 4/2003 | Chekanov |
| 6,567,699 | B2 | 5/2003 | Alferness et al. |
| 6,587,734 | B2 | 7/2003 | Okuzumi |
| 6,595,912 | B2 | 7/2003 | Lau et al. |
| 6,602,184 | B2 | 8/2003 | Lau et al. |
| 6,604,529 | B2 | 8/2003 | Kim |
| 6,612,979 | B2 | 9/2003 | Lau et al. |
| 6,622,979 | B2 | 9/2003 | Valiulis |
| 6,629,921 | B1 | 10/2003 | Schweich, Jr. et al. |
| 6,645,139 | B2 | 11/2003 | Haindl |
| 6,663,558 | B2 | 12/2003 | Lau et al. |
| 6,673,009 | B1 | 1/2004 | Vanden Hoek et al. |
| 6,682,474 | B2 | 1/2004 | Lau et al. |
| 6,689,048 | B2 | 2/2004 | Vanden Hoek et al. |
| 6,702,732 | B1 | 3/2004 | Lau et al. |
| 6,720,402 | B2 | 4/2004 | Langer et al. |
| 6,723,038 | B1 | 4/2004 | Schroeder et al. |
| 6,723,041 | B2 | 4/2004 | Lau et al. |
| 6,746,471 | B2 | 6/2004 | Mortier et al. |
| 6,755,777 | B2 | 6/2004 | Schweich, Jr. et al. |
| 6,755,779 | B2 | 6/2004 | Vanden Hoek et al. |
| 2002/0065373 | A1 | 5/2002 | Krishnan |
| 2002/0161114 | A1 | 10/2002 | Gunatillake et al. |
| 2002/0188170 | A1 | 12/2002 | Santamore et al. |
| 2003/0078671 | A1 | 4/2003 | Lesnaik et al. |
| 2003/0199974 | A1 | 10/2003 | Lee et al. |
| 2003/0233045 | A1 | 12/2003 | Vaezy |
| 2004/0002626 | A1 * | 1/2004 | Feld et al. ............... 600/37 |
| 2004/0014929 | A1 | 1/2004 | Lendlein et al. |
| 2004/0015187 | A1 | 1/2004 | Lendlein et al. |
| 2004/0098121 | A1 | 5/2004 | Opolski |
| 2004/0116945 | A1 | 6/2004 | Sharkawy et al. |
| 2004/0234453 | A1 | 11/2004 | Smith |
| 2004/0260393 | A1 | 12/2004 | Rahdert et al. ............ 623/2.36 |

OTHER PUBLICATIONS

Cohen-Karni et al., "Fe-Pd Alloy Ferromagnetic Shape Memory Thin Films," Research Experience for Undergraduates Project, Harvard University, 2003, 31 pages.

Lendlein et al., Biodegradable, Elastic Shape-Memory Polymers for Potential Biomedical Applications, *Science*, vol. 296 (May 31, 2002), pp. 1673-1676.

Li, Studies on Thermally Stimulated Memory Effect of Segmented Polyurethanes, *J Appl Plym Sci*, (1997) 64: 1511-1516.

Oikawa, Development of Co-Ni-Al-based Ferromagnetic Shape Memory Alloys, *AIST Today*, vol. 1, No. 7 (2001), pp. 18.

Tellinen et al., "Basic Properties of Magnetic Shape Memory Actuators," Published in 8th International Conference Actuator, Bremen, Germany, Jun. 2002, pp. 10-12.

* cited by examiner

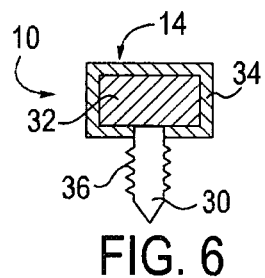 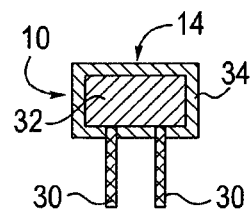 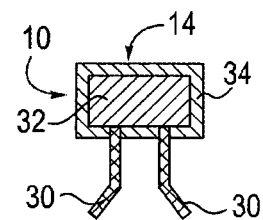
FIG. 6  FIG. 8A  FIG. 8B
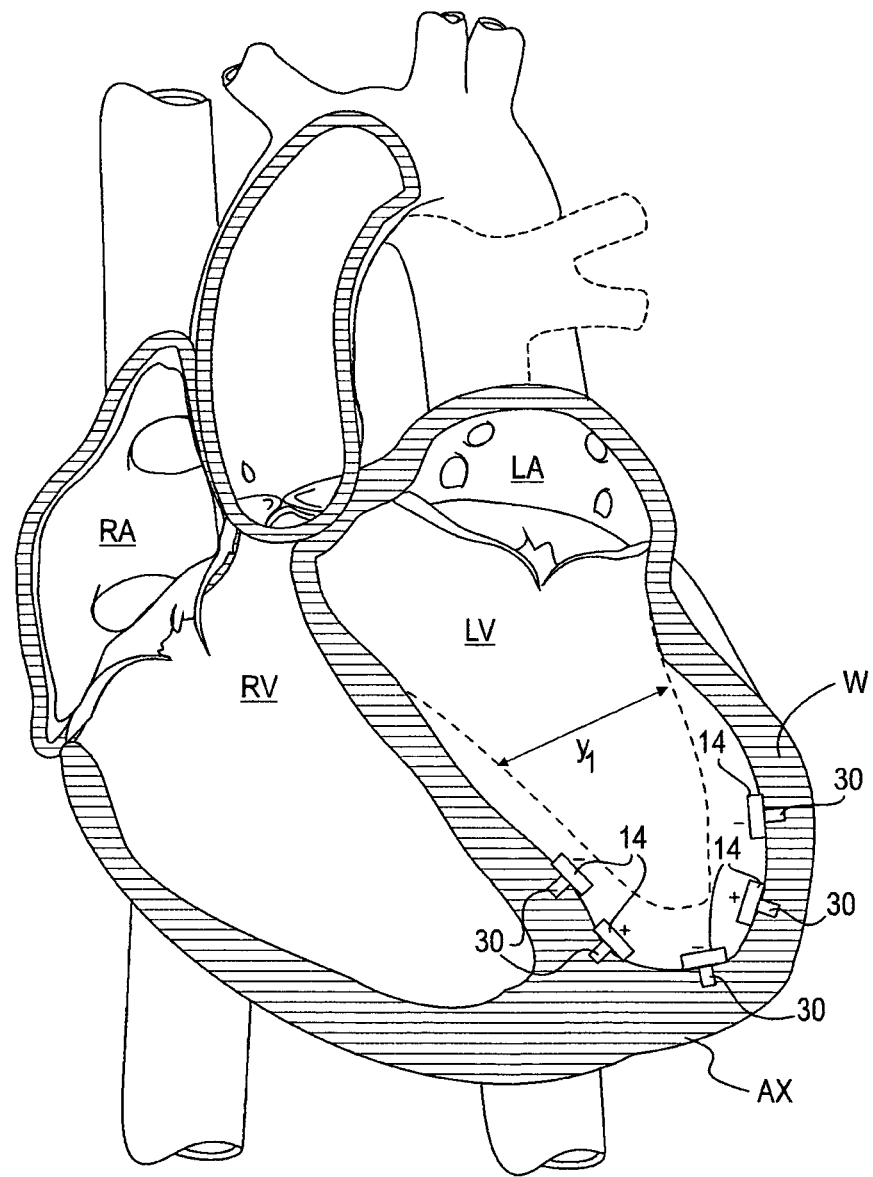
FIG. 7

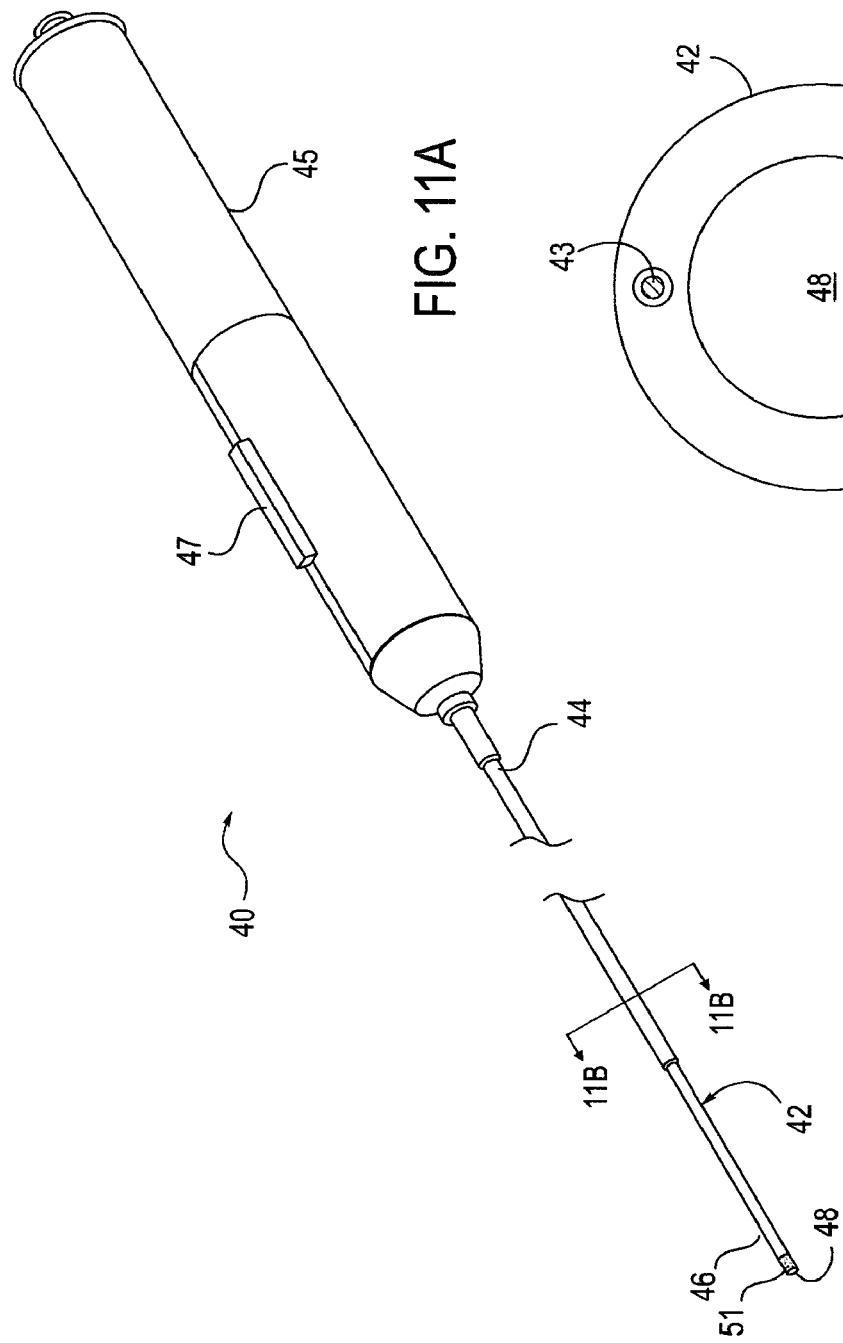
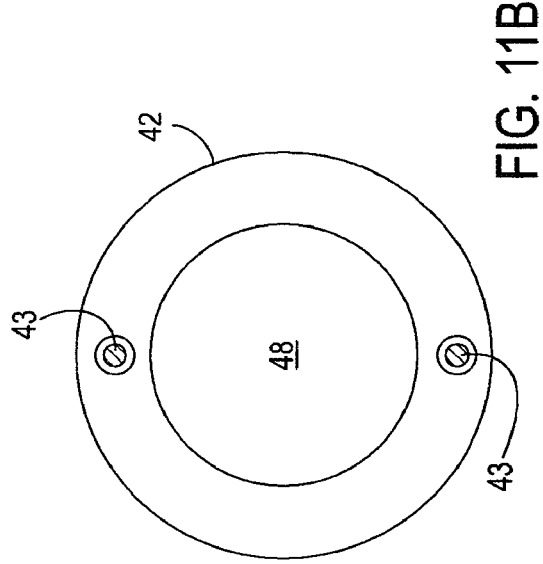

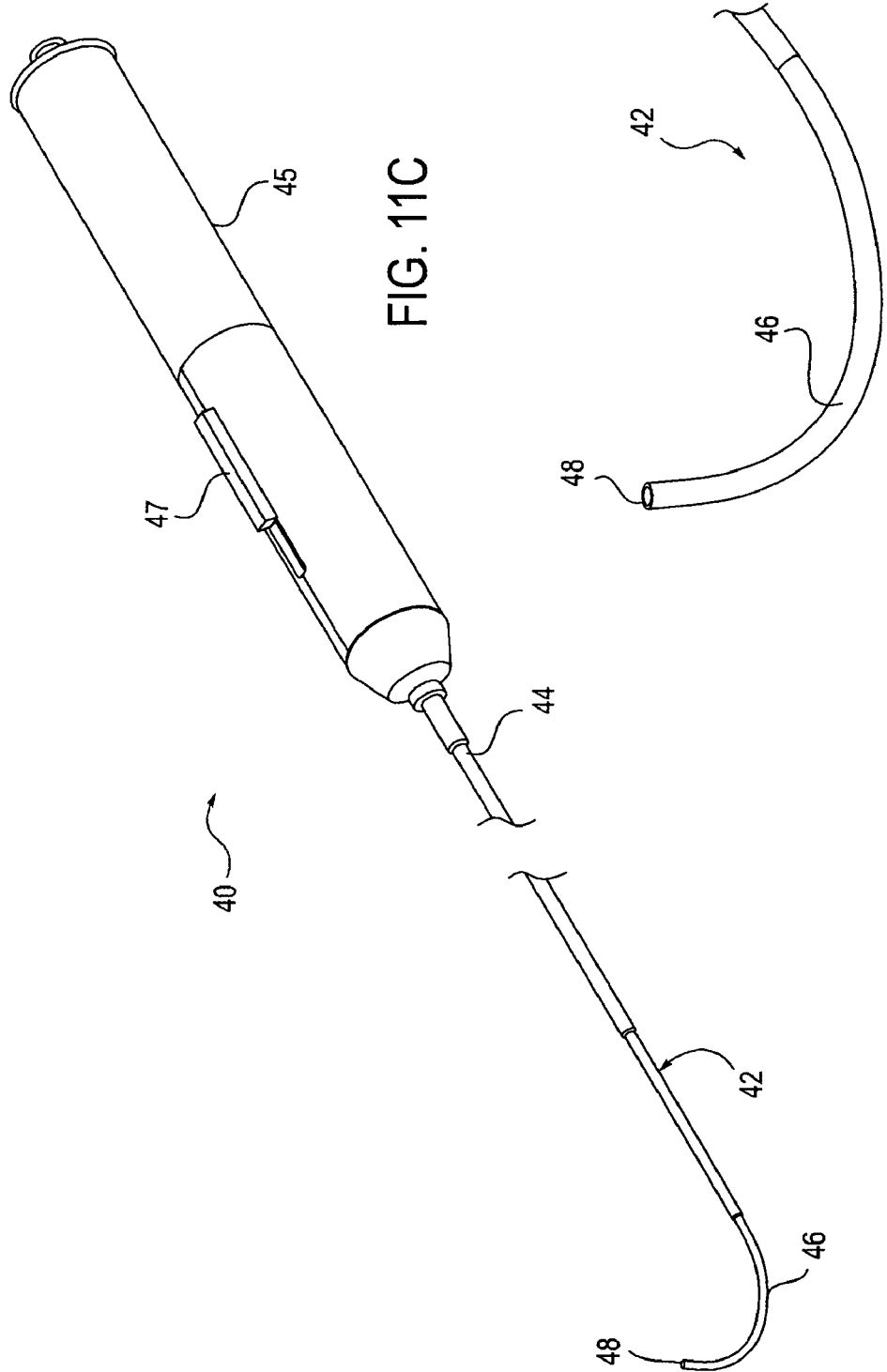

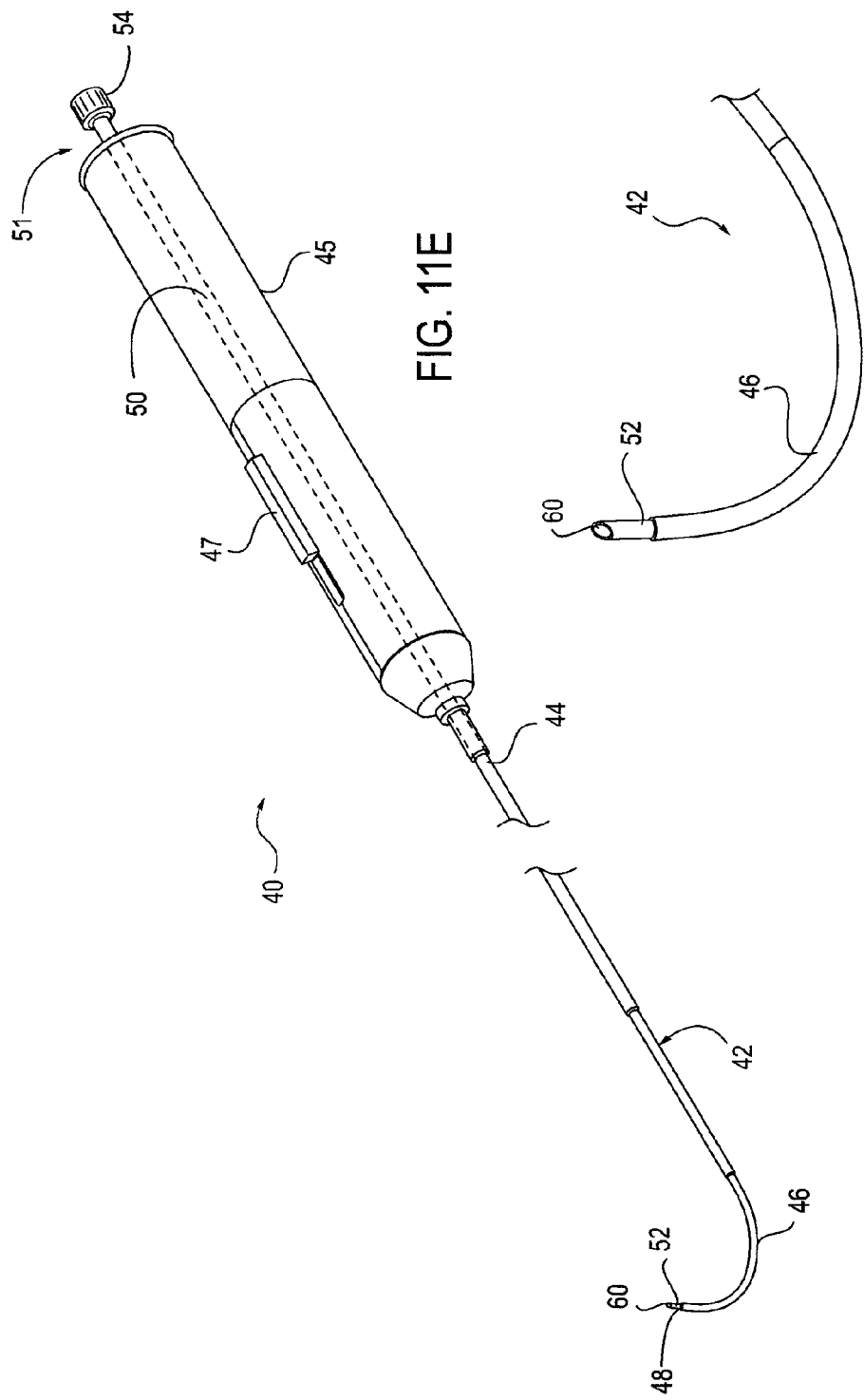

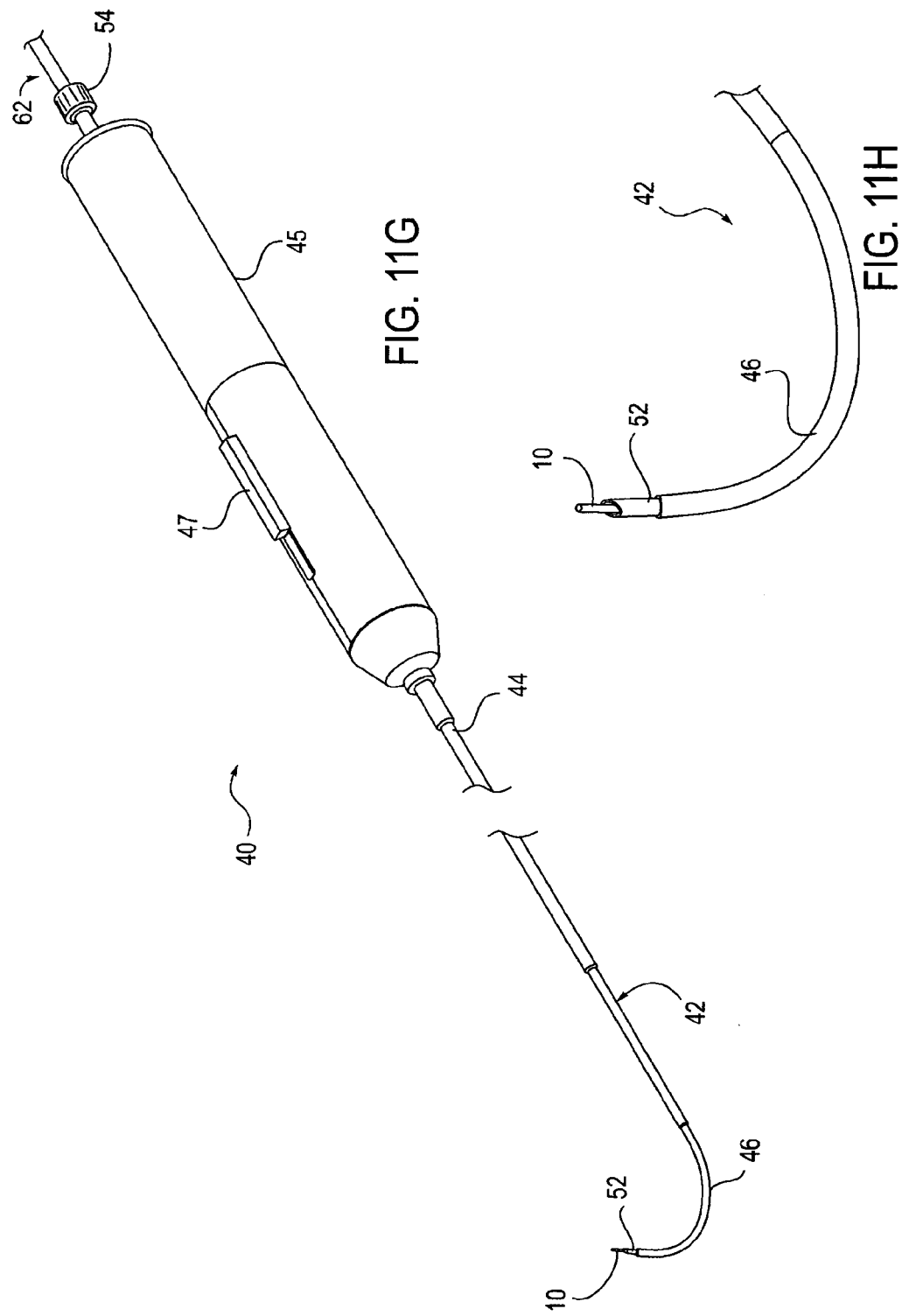

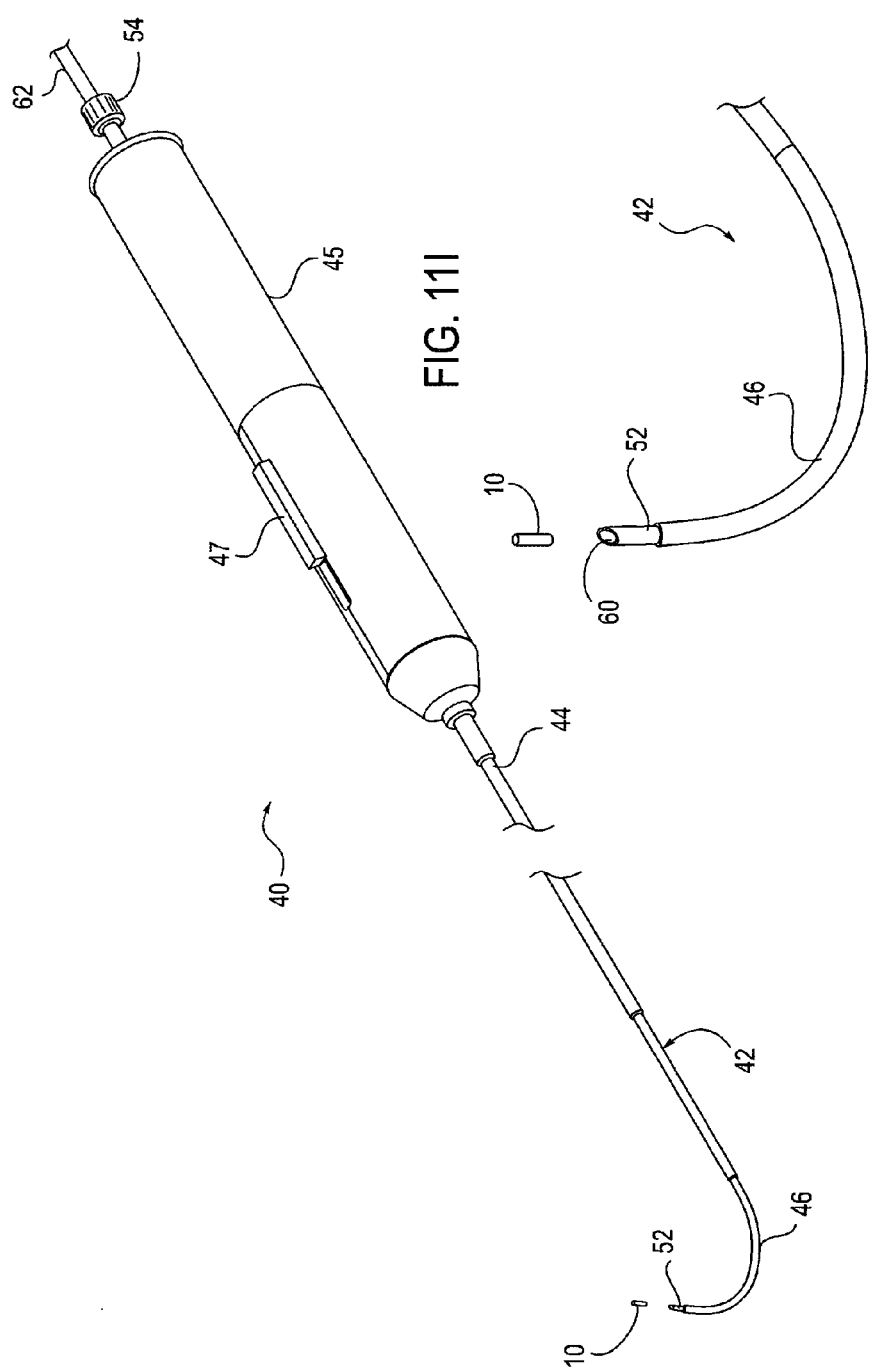

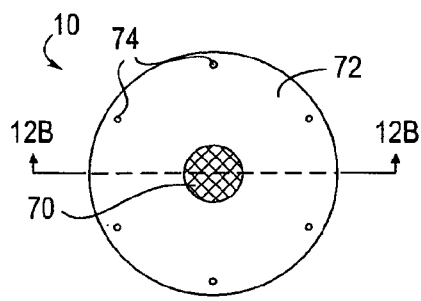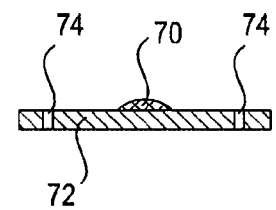
FIG. 14A  FIG. 14B
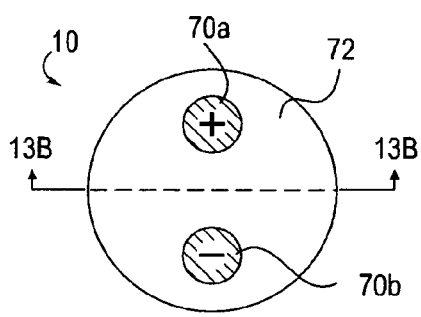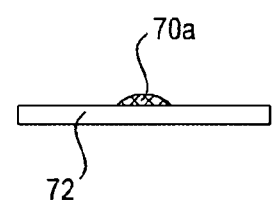
FIG. 15A  FIG. 15B
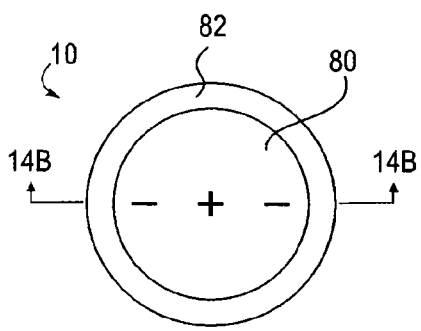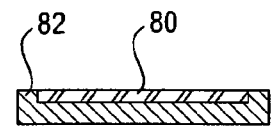
FIG. 16A  FIG. 16B

MAGNETIC DEVICES AND METHODS FOR RESHAPING HEART ANATOMY

CROSS-REFERENCES TO RELATED APPLICATIONS

This application claims the priority of U.S. Provisional Patent Application No. 60/588,254, filed on Jul. 15, 2004, incorporated herein by reference for all purposes.

This application is also related to U.S. patent application Ser. No. 11/142,078 now U.S. Pat. No. 7,285,087, filed on the same day as the instant application and incorporated herein by reference for all purposes.

STATEMENT AS TO RIGHTS TO INVENTIONS MADE UNDER FEDERALLY SPONSORED RESEARCH OR DEVELOPMENT

Not applicable

REFERENCE TO A "SEQUENCE LISTING," A TABLE, OR A COMPUTER PROGRAM LISTING APPENDIX SUBMITTED ON A COMPACT DISK.

Not applicable

BACKGROUND OF THE INVENTION

Heart failure is a common course for the progression of many forms of heart disease. Heart failure may be considered to be the condition in which an abnormality of cardiac function is responsible for the inability of the heart to pump blood at a rate commensurate with the requirements of the metabolizing tissues, or can do so only at an abnormally elevated filling pressure. There are many specific disease processes that can lead to heart failure, many of which are not fully known. In certain instances, heart disease may result from viral infections. In such cases, the heart may enlarge to such an extent that the adverse consequences of heart enlargement continue after the viral infection has passed and the disease continues its progressively debilitating course. In other cases, the initial cause is due to chronic hypertension, myocardial infarction, mitral valve incompetency, or other dilated cardiomyopathies. With each of these conditions, the heart is forced to overexert itself in order to provide the cardiac output demanded by the body during its various demand states. The result is dilation of the left ventricle and remodeling of the heart tissues.

Remodeling involves physical changes to the size, shape and thickness of the heart wall along with a neurohormonal milieu of the entire cardiovascular system. A damaged left ventricle may have some localized thinning and stretching of a portion of the myocardium. The thinned portion of the myocardium often is functionally impaired, and other portions of the myocardium attempt to compensate. As a result, the other portions of the myocardium may expand so that the stroke volume of the ventricle is maintained notwithstanding the impaired zone of the myocardium. Such expansion may cause the left ventricle to assume a somewhat spherical shape.

Cardiac remodeling often subjects the heart wall to increased wall tension or stress, which further impairs the heart's functional performance. Often, the heart wall will dilate further in order to compensate for the impairment caused by such increased stress. If dilation exceeds a critical value, the result will be progressive heart dilation which can be explained by Laplace's law. As the volume subtended by the left hear chamber increases, the stresses in the walls of this cavity will increase. Consequently, the muscle fibrils are overloaded and their ideal range of elongation is exceeded. When this excessive elongation takes place, there is a residual volume in the heart. Then the muscle fibrils must operate against a primarily high wall strain, and are further extended. A vicious cycle arises, leading to increasing distension of the heart and consequent heart insufficiency.

Heart transplantation is one surgical procedure used for treatment of heart failure. Unfortunately, not enough hearts are available for transplant to meet the needs of heart failure patients. In the United States, in excess of 35,000 transplant candidates compete for only about 2,000 transplants per year. A transplant waiting list is about 8-12 months long on average and frequently a patient may have to wait about 1-2 years for a donor heart. While the availability of donor hearts has historically increased, the rate of increase is slowing dramatically. Even if the risks and expense of heart transplant could be tolerated, this treatment option is becoming increasingly unavailable. Further, many patients do not qualify for heart transplant for failure to meet any one of a number of qualifying criteria.

Consequently, substantial effort has been made to find alternative treatments for heart failure. One such surgical treatment is referred to as the Batista procedure; the surgical technique includes dissecting and removing portions of the heart in order to reduce heart volume. This is a radical and experimental procedure subject to substantial controversy. Furthermore, the procedure is highly invasive, risky and expensive and commonly includes other expensive procedures (such as a concurrent heart valve replacement). And if the procedure fails, emergency heart transplant is the only available option.

Another surgical treatment is dynamic cardiomyoplasty. In this procedure, the latissimus dorsi muscle (taken from the patient's shoulder) is wrapped around the heart and chronically paced synchronously with ventricular systole. Pacing of the muscle results in muscle contraction to assist the contraction of the heart during systole. Even though cardiomyoplasty has demonstrated symptomatic improvement, studies suggest the procedure only minimally improves cardiac performance. In addition, the procedure is highly invasive requiring harvesting a patient's muscle and an open chest approach (i.e., sternotomy) to access the heart. Furthermore, the procedure is expensive, especially for those using a paced muscle which require costly pacemakers. The cardiomyoplasty procedure is also complicated. For example, it is difficult to adequately wrap the muscle around the heart with a satisfactory fit. Also, if adequate blood flow is not maintained to the wrapped muscle, the muscle may necrose. The muscle may stretch after wrapping reducing its constraining benefits and is generally not susceptible to post-operative adjustment. Finally, the muscle may fibrose and adhere to the heart causing undesirable constraint on the contraction of the heart during systole.

A variety of devices have also been developed to treat heart failure by improving cardiac output. For example, left ventricular assist pumps have been developed to help the heart to pump blood. These mechanical pumps reduce the load on the heart by performing all or part of the pumping function normally done by the heart. Currently, mechanical pumps are used to sustain the patient while a donor heart for transplantation becomes available for the patient. Researchers and cardiac surgeons have also experimented with prosthetic "girdles" disposed around the heart. One such design is a prosthetic "sock" or "jacket" that is wrapped around the heart.

However, these designs require invasive open chest surgery, significant handling of the heart, and have not seen widespread success.

Consequently, there is a need for alternative treatments applicable to both early and later stages of heart failure to correct pumping insufficiency due to distension of the heart thereby stopping the progressive nature of the disease or more drastically slowing the progressive nature of congestive heart disease. It is also desired that such therapies require minimal manipulation of the heart, be available to a broad spectrum of patients with various degrees of heart failure, be cost effective, safe and efficient. At least some of these objectives will be met with the present invention.

BRIEF SUMMARY OF THE INVENTION

Systems, methods and devices are provided for treating heart failure patients suffering from various levels of heart dilation. Heart dilation treated by reshaping the heart anatomy with the use of magnetic forces. Such reshaping changes the geometry of portions of the heart, particularly the right or left ventricles, to increase contractibility of the ventricles thereby increasing the stroke volume which in turn increases the cardiac output of the heart. The magnetic forces are applied with the use of one or more magnetic elements which are implanted within the heart tissue or attached externally and/or internally to a surface of the heart. The various charges of the magnetic forces interact causing the associated heart tissue areas to readjust position, such as to decrease the width of the ventricles. Such repositioning is maintained over time by the force of the magnetic elements, allowing the damaging effects of heart dilation to slow in progression or reverse.

In a first aspect of the present invention, methods are provided for reshaping the heart anatomy. In one embodiment, the method includes implanting a first magnetic element having a first charge at least partially within a first tissue area of the heart anatomy, and implanting a second magnetic element having a second charge at least partially within a second tissue area of the heart anatomy. The first and second magnetic elements are arranged so as to magnetically interact with each other causing at least one of the first and second tissues areas to move in a manner which reshapes the heart anatomy. For example, when the first and second magnetic elements have opposite charges, the magnetic elements may be arranged so as to magnetically attract each other. This causes at least one of the first and second tissue areas to move toward the other. When the magnetic elements are implanted on opposite sides of a ventricle, movement of the tissues toward each other may draw the tissues inward and reduce the width of the ventricle. When the first and second magnetic elements have similar charges, the magnetic elements may be arranged so as to magnetically repel each other. This causes at least one of the first and second tissue areas to move away from the other. Depending on the initial geometry of the heart anatomy, movement of specific tissue areas away from each other may cause other areas to move toward each other. The overall result may thus be reduced dilation.

Typically, the method further comprises implanting a third magnetic element having a third charge at least partially within a third tissue area of the heart anatomy. The third magnetic element is positioned so as to magnetically interact with the first and/or second magnetic element causing at least one of the first, second and third tissues areas to move in a manner which reshapes the heart anatomy.

In preferred embodiments, least one of the first tissue area and the second tissue area comprise a wall of a ventricle and reshaping the heart anatomy comprises reshaping the ventricle. Typically, reshaping the ventricle comprises drawing at least one wall of the ventricle inward reducing a width of the ventricle. However, it may be appreciated that the tissue areas may be at any location, including the right atrium, left atrium, the valves, and/or any of the associated anatomy, such as the aorta, pulmonary artery, pulmonary vein, chordae, etc.

In some embodiments, the first magnetic element includes at least one protrusion and implanting the first magnetic element comprises advancing at least a portion of the at least one protrusion at least partially within the first tissue area of the heart anatomy. When the at least one has a screw shape, advancing at least a portion of the protrusion may include rotating the screw shape. In other embodiments, the at least one protrusion is capable of bending, typically to help anchor the magnetic element in the tissue. Such bending may be achieved by applying energy to the protrusion which causes the bending. Such energy may include an electrical current, external energy or a combination of these.

In another embodiment, the method of reshaping the heart anatomy comprises attaching a first magnetic element having a first charge to a first target location on a surface of the heart anatomy, and attaching a second magnetic element having a second charge to a second target location on a surface of the heart anatomy. The first and second magnetic elements are arranged so as to magnetically interact with each other causing the first and second target locations to move in a manner which reshapes the heart anatomy. When the first and second charges are opposite charges, the magnetic elements may be arranged so as to magnetically attract causing the at least one of the first and second target locations move toward the other. And, when the first and second charges are similar charges and the magnetic elements may be arranged so as to magnetically repel causing the at least one of the first and second target locations to move away from the other.

Typically, the method further comprises attaching a third magnetic element having a third charge to a third target location on a surface of the heart anatomy, wherein the third magnetic element is positioned so as to magnetically interact with the first and/or second magnetic element causing at least one of the first, second and third target locations to move in a manner which reshapes the heart anatomy.

In preferred embodiments, least one of the first target location and the second location are on a wall of a ventricle and reshaping the heart anatomy comprises reshaping the ventricle. Typically, reshaping the ventricle comprises drawing at least one wall of the ventricle inward reducing a width of the ventricle. However, it may be appreciated that the target locations may be at any location, including the right atrium, left atrium, the valves, and/or any of the associated anatomy, such as the aorta, pulmonary artery, pulmonary vein, chordae, etc. In addition, at least one of the first target location and the second location may be on an external surface of the heart anatomy. Likewise, at least one of the first target location and the second location may be on an internal surface of the heart anatomy. Attaching the first magnetic element may include adhering the first magnetic element to the first target location on a surface of the heart anatomy with adhesive.

In some embodiments, the first magnetic element includes a patch and attaching the first magnetic element comprises attaching the patch to the first target location on a surface of the heart anatomy. Attaching the patch may include, for example, suturing or adhering the patch to the first target location on a surface of the heart anatomy.

In another aspect of the present invention, a magnetic element is provided for reshaping heart anatomy. In some embodiments, the magnetic element comprises a magnetic core, and at least one protrusion adapted to be at least partially implantable within a tissue area of the heart anatomy. The magnetic core is comprised of any suitable magnetic material, such as Neudynium Iron Boron, Samarium Cobalt, Aluminum Nickel Cobalt or a combination of these. Likewise, the at least one protrusion may be comprised of any suitable material including a shape memory material. In the instance of a shape memory material, the protrusion may form a bend upon receiving energy which anchors the at least one protrusion within the tissue area of the heart anatomy. In other embodiments, the at least one protrusion has the shape of a screw. In addition, the magnetic core may include a biocompatible polymer coating.

In a further aspect of the invention, a composite magnetic element is provided for reshaping heart anatomy. In some embodiments, the composite magnetic element comprises a core inner layer comprising magnetic material and at least one outer layer comprising a non-magnetic material attached to the core inner layer. In preferred embodiments, the at least one outer layer comprises two outer layers, wherein the core inner layer is sandwiched between the outer layers. The magnetic material of the core inner layer may be comprised of any suitable magnetic material, including Neudynium Iron Boron, Samarium Cobalt, Aluminum Nickel Cobalt or a combination of these. The non-magnetic material of the at least one outer layer may be metallic or non-metallic and may be comprised of stainless steel, platinum, iridium, titanium, or tantalum, to name a few. In addition, the composite magnetic element may further include a biocompatible polymer coating.

In another aspect of the invention, a system of magnetic elements is provided for reshaping heart anatomy. In one embodiment, the system includes a first magnetic element having a first charge and a second magnetic element having a second charge. The first magnetic element is adapted to be at least partially implantable within or positionable on a first tissue area of the heart anatomy and the second magnetic element is adapted to be at least partially implantable within or positionable on a second tissue area of the heart anatomy. The first and second magnetic elements are arrangeable so as to magnetically interact with each other causing at least one of the first and second tissues areas to move in a manner which reshapes the heart anatomy. In some embodiments, at least one of the magnetic elements has the shape of discs, cones, rods, blocks, spheres, rings or a combination of these. And, in some embodiments, at least one of the magnetic elements comprises a composite magnetic element including a core inner layer of magnetic material and at least one outer layer comprised of a non-magnetic material attached to the core inner layer. Further, in some embodiments, at least one of the magnetic elements includes a protrusion that is at least partially implantable within the associated tissue area of the heart anatomy.

In another aspect of the present invention, a delivery system is provided for delivering a magnetic element. In some embodiments, the delivery system includes a catheter having a proximal end and a distal end, a needle having a passageway extending therethough, the needle being advanceable through the catheter and having a needle tip which is extendable beyond the distal end of the catheter, and a least one magnetic element configured for passage through the passageway and delivery from the needle tip. The system may further comprise a stylet advanceable through the passageway to pass the at least one magnetic element therethrough. The system may also comprise a needle advancement mechanism which advances and retracts the needle tip in relation to the distal end of the catheter. As stated previously, the at least one magnetic element may have the shape of a disc, cone, rod, block, sphere, ring or a combination of these, to name a few.

Other objects and advantages of the present invention will become apparent from the detailed description to follow, together with the accompanying drawings.

BRIEF DESCRIPTION OF THE DRAWINGS

FIG. 6 illustrate an embodiment of a magnetic element having a protrusion in the shape of a screw.

FIG. 7 illustrates magnetic elements having protrusions anchored to the walls of the left ventricle.

FIGS. 8A-8B illustrate magnetic elements having protrusions for anchoring.

FIGS. 11A-11J illustrates an embodiment of a delivery system.

FIGS. 14A-14B, 15A-15B, 16A-16B illustrate embodiments of magnetic elements including patches.

DETAILED DESCRIPTION OF THE INVENTION

Figure 2:
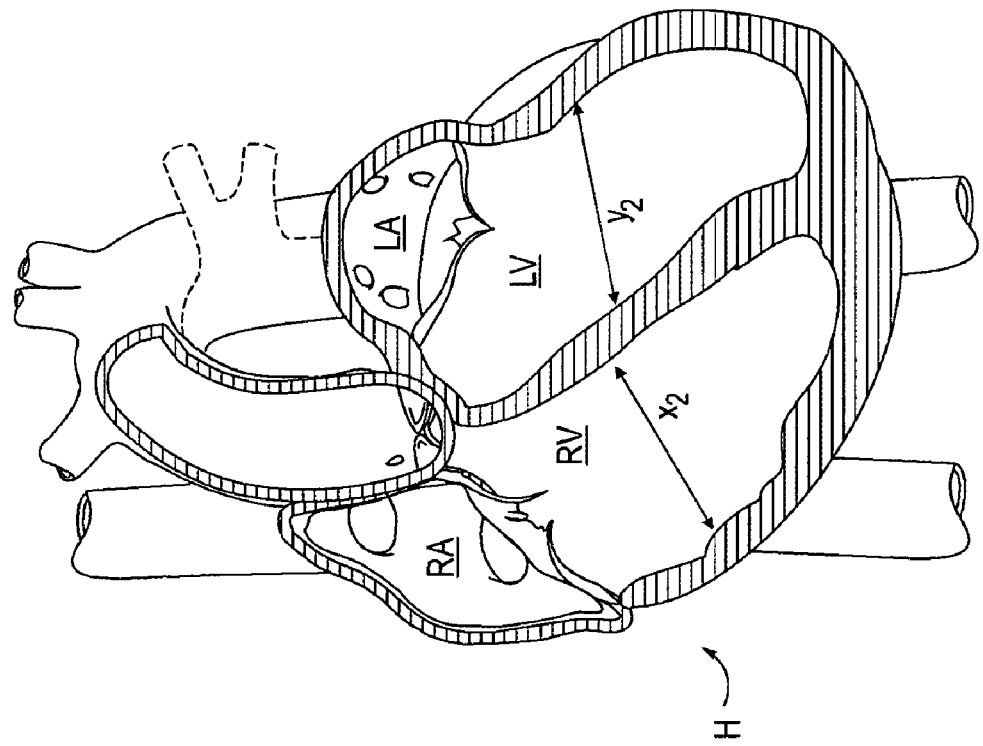
FIG. 2 provides a cross-sectional illustration of a heart of a patient wherein the geometry of the ventricles have dilated.
Figure 1:
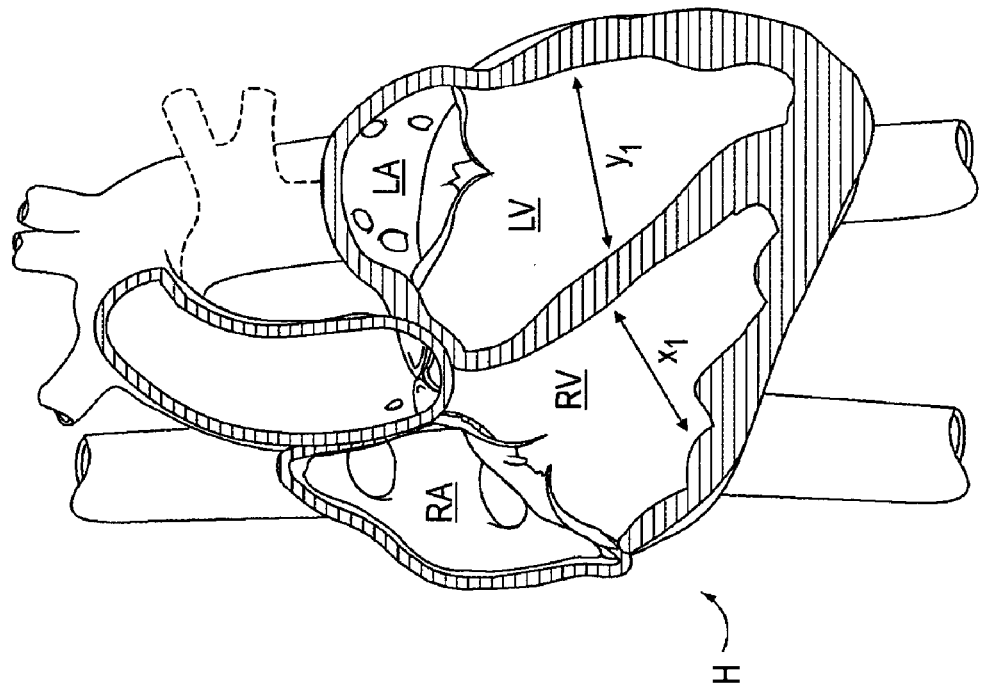
FIG. 1 provides a cross-sectional illustration of a heart of a normal patient.

FIG. 1 provides a cross-sectional illustration of a heart H of a normal patient. The cross-sectional view shows the right atrium RA, right ventricle RV, left atrium LA and left ventricle LV. The right ventricle RV and left ventricle LV have a width of $x_1$ and $y_1$ respectively. FIG. 2 provides a cross-sectional illustration of a heart H of a patient with heart disease wherein the geometry of the ventricles RV, LV have dilated. As shown, the right ventricle RV and left ventricle LV have increased widths of $x_2$ and $y_2$ respectively. The increased widths $x_2, y_2$ result in poor cardiac output from the left ventricle LV and/or the right ventricle RV. Cardiac output (CO) is defined as:

$$CO = HR \times SV$$

whereas

HR=heart rate (beats per minute)

SV=stroke volume (liters per beat)

Ejection Fraction (EF) is the fraction of blood ejected by a ventricle relative to its end-diastolic volume. Therefore, EF is calculated from:

$$EF = (SV/EDV) \times 100$$

whereas

EDV=end-diastolic volume

Ejection fraction is most commonly measured using echocardiography. This non-invasive technique provides good estimates of end-diastolic (EDV) and end-systolic volumes (ESV), and stroke volume (SV=EDV−ESV). Normally, EF is >60%. For example, if the SV is 75 ml and the EDV is 120 ml, then the EF is 63%. Factors effecting EDV are heart rate, ventricular compliance and filling pressure. Factors effecting ESV are the force of contracting the left ventricle and after-load which is the measure of the force resulting from the ejection of blood.

In heart failure, particularly in dilated cardiomyopathy, EF can become very small as SV decreases and EDV increases. In severe heart failure, EF may be only 20%. EF is often used as a clinical index to evaluate the status of the heart. By changing the geometry or reshaping the left or right ventricle with the methods and devices of the present invention, the contractibility of the ventricles may be increased thereby increasing the stroke volume (SV). This in turn increases the cardiac output (CO).

Figure 3:
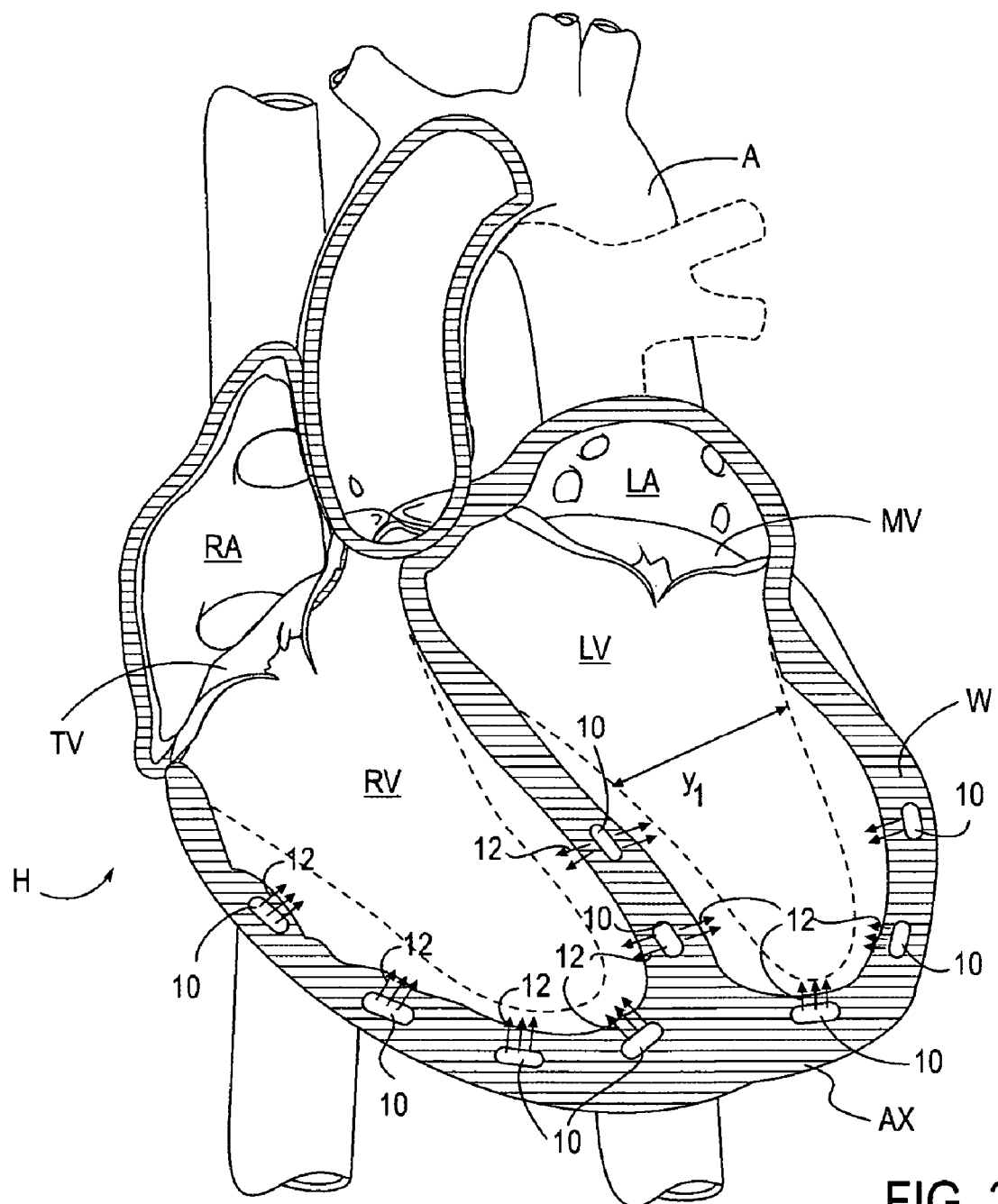
FIG. 3 illustrates changing of the geometry of the ventricles of FIG. 2 by placing magnetic elements within the walls of the ventricles.

The geometry of the ventricles are changed by placing magnetic elements 10 on or within tissue areas or walls W of the ventricles, such as illustrated in FIG. 3. In the embodiment of FIG. 3, magnetic elements 10 are implanted within the walls W of the right ventricle RV and left ventricle LV near the apex AX of the heart H. The magnetic elements 10 have opposing poles so that the magnetic elements 10 attract each other, as indicated by arrows 12. Such attraction draws the walls W of the ventricles RV, LV inward, toward each other, thereby reshaping the ventricles RV, LV. The width of the right ventricle RV is thus reduced toward normal width $x_1$ and the left ventricle LV is reduced toward the normal width $y_1$. The magnetic forces are able to assist the ventricles RV, LV throughout the cardiac cycle, increasing the contractibility of the ventricles RV, LV. This increases the stroke volume (SV) which increases the cardiac output (CO). It may be appreciated that any number of elements 10 may be used and the elements 10 may be positioned at any location on (externally or internally) or within the walls W of the heart H, including the right atrium RA, right ventricle RV, left atrium LA and left ventricle LV. It may further be appreciated the elements 10 may be positioned on or within the valves, including the mitral valve MV, aortic valve AV, tricuspid valve TV, and pulmonary valve (not shown), and/or any of the associated anatomy, such as the aorta A, pulmonary artery, pulmonary vein, chordae etc.

Figure 4A:
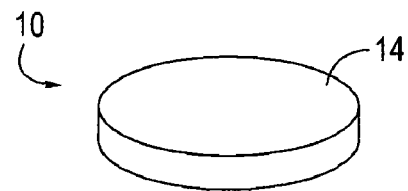
FIGS. 4A-4C illustrate an embodiment of a magnetic disc of the present invention.
Figure 4B:
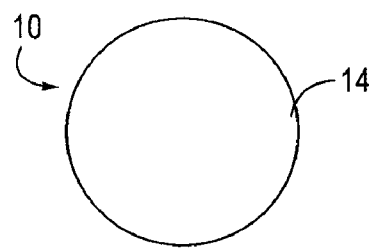
Figure 4C:
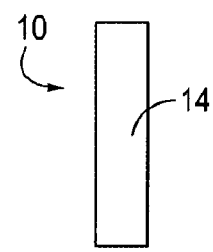

The magnetic elements 10 are comprised of any suitable magnetic material, such as Neudynium Iron Boron (Nd Fe B), Samarium Cobalt (Sm Co) or Aluminum Nickel Cobalt (Al Ni Co). The magnetic elements 10 may have any suitable size and shape, including discs, cones, rods, blocks, spheres, and rings to name a few. In one embodiment, illustrated in FIGS. 4A-4C, the magnetic element 10 has the shape of disc 14. FIG. 4A provides a perspective view of the magnetic disc 14. FIG. 4B illustrates a top view having a circular shape with a diameter in the range of approximately 0.1-3 mm. FIG. 4C illustrates a side view wherein the disc 14 has a thickness in the range of approximately 0.1-3 mm. These magnetic discs 14 can provide forces in the range of approximately 0.2-0.5 lbf with a magnetic field in the range of 300-7000 Gauss. In addition, the discs 14 may be coated with a biocompatible polymer, such as polyurethane, polytetrafluoroethylene (PTFE), fluorinated ethylene propylene (FEP) or polyether ether ketone (PEEK). Typically, such a coating has a thickness in the range of approximately 0.1-0.3 mm.

Figure 5A:
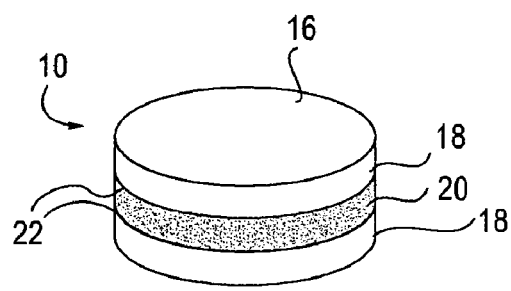
FIGS. 5A-5C illustrate another embodiment of a magnetic disc of the present invention.
Figure 5B:
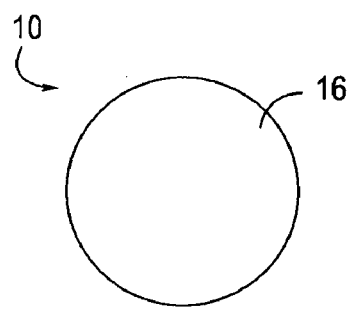
Figure 5C:
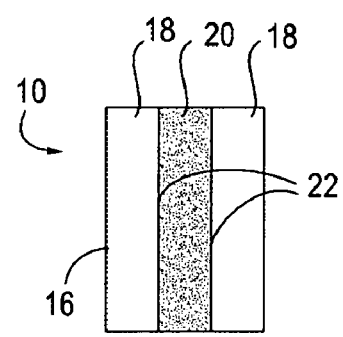

In another embodiment, illustrated in FIGS. 5A-5C, the magnetic element 10 has the form of a composite magnetic disc 16. Here, the composite magnetic disc 16 is comprised of a core inner layer 18 and two outer layers 20. The core inner layer 18 is comprised of any suitable magnetic material, such as Neudynium Iron Boron (Nd Fe B), Samarium Cobalt (Sm Co) or Aluminum Nickel Cobalt (Al Ni Co), and has a thickness in the range of approximately 0.1-3 mm. The outer layers 20 are comprised of any suitable non-magnetic material, such as 316L stainless steel, and have a thickness of approximately 0.1 mm. The outer layers 20 are joined with the core inner layer 18 with a suitable adhesive 22, such as cyanoacrylate or epoxy.

FIG. 5A provides a perspective view of the composite magnetic disc 16. FIG. 5B illustrates a top view having a circular shape with a diameter in the range of approximately 0.1-3 mm. FIG. 5C illustrates a side view wherein the disc 16 has a thickness in the range of approximately 0.1-3 mm. The composite magnetic discs 16 provide a less brittle magnet and an increased force of attraction. In addition, the discs 16 may also be coated with a biocompatible polymer, such as polyurethane, polytetrafluoroethylene (PTFE), fluorinated ethylene propylene (FEP) or polyether ether ketone (PEEK). Typically, such a coating has a thickness in the range of approximately 0.1-0.3 mm.

It may be appreciated that the magnetic elements of the present invention may have the form of a rod. In some embodiments, the rod has a diameter in the range of approximately 0.1-3 mm and a length in the range of 3-8 mm. Similar to the magnetic discs described above, the rod may be comprised of any suitable magnetic material, such as Neudynium Iron Boron (Nd Fe B), Samarium Cobalt (Sm Co) or Aluminum Nickel Cobalt (Al Ni Co), to name a few. Likewise, the rod may include a biocompatible polymer coating 34, such as polyurethane, polytetrafluoroethylene (PTFE), fluorinated ethylene propylene (FEP) or polyether ether ketone (PEEK), having a thickness in the range of 0.1-0.3 mm.

As previously mentioned, the magnetic elements 10 may be positioned at any location on (externally or internally) or within the walls W of the heart H. When the elements 10 are positioned within the walls W, the elements 10 are advanced through at least a portion of the wall W with the use of a delivery instrument, as will be described in later sections, so that the elements 10 are substantially surrounded by the tissue of the walls W and therefore held in place by the tissue of the walls W. When the elements 10 are positioned on the walls W, the elements 10 are held in place by adhesion to the surface of the walls W or by anchoring into the walls W, such as by suturing or advancing one or more protrusions into the walls W. For example, FIGS. 6, 8A-8B illustrate embodiments of magnetic elements 10 having protrusions 30 suitable for advancement into the walls W. In FIG. 6, the magnetic element 10 comprises a magnetic disc 14, such as the magnetic disc 14 of FIGS. 4A-4C having a core 32 of suitable magnetic material, and a protrusion 30 having the shape of a screw. The screw shape includes threads 36 so that the protrusion 30 may be advanced through the tissue of the ventricle wall W and held in place. The disc 14 and protrusion 30 may be joined by any suitable means, such as by an adhesive or a mechanical attachment mechanism. It may also be appreciated that the disc 14 and protrusion 30 may be formed as a continuous unit. The disc 14 is also typically covered by a biocompatible polymer coating 34, such as polyurethane, polytetrafluoroethylene (PTFE), fluorinated ethylene propylene (FEP) or polyether ether ketone (PEEK). The protrusion 30 may be comprised of any suitable material, such as stainless steel. Further, the protrusion 30 may be plated or coated with a material to provide desired physical characteristics. For example, if the disc 14 and protrusion 30 are formed as one unit of magnetic material, the protrusion 30 may be coated with stainless steel to reduce brittleness. It may also be appreciated that magnetic discs 10 of any shape and composition may have protrusions 30, including the magnetic disc 16 of FIGS. 5A-5C.

Referring to FIG. 7, magnetic elements 10 having protrusions 30 are illustrated anchored to the walls W of the left ventricle LV. Here, five magnetic elements 10 are shown near the apex AX of the heart H. The protrusions 30 are advanced into the ventricular tissue of the walls W so that the discs 14 are disposed on the interior surface of the left ventricle LV. The magnetic elements 10 have opposing poles so that the magnetic elements 10 attract each other. Such attraction draws the walls W of the left ventricle LV inward, toward each other, thereby reshaping the left ventricle LV. The width of the left ventricle LV is thus reduced toward the normal width $y_i$. The magnetic forces are able to assist the left ventricle LV throughout the cardiac cycle, increasing the contractibility of the LV ventricle. This increases the stroke volume (SV) which increases the cardiac output (CO).

Additional embodiments of magnetic elements 10 having protrusions 30 for anchoring are shown in FIGS. 8A-8B. In FIG. 8A, the magnetic element 10 comprises a magnetic disc 14, such as the magnetic disc 14 of FIGS. 4A-4C having a core 30 of suitable magnetic material, and at least one protrusion 30. The protrusions 30 are directly advanceable into the ventricular tissue of the wall W. To hold the magnetic elements 10 in place, the protrusions 30 are then curved, bowed or bent, as illustrated in FIG. 8B. Such bending may be achieved by a variety of mechanisms. For example, the protrusions 30 may be comprised of a shape memory material, such as Nickel Titanium (also known as Nitinol®), wherein the change in shape is achieved by applying an electrical current, such as a DC voltage or radiofrequency, or by applying external energy, such as a magnetic field using a clinically available magnetic resonance imaging machine or high intensity focused ultrasound. Such application raises the temperature of the shape memory material from 37° C. to a transition temperature of 45-50° C. wherein bending occurs. The bent protrusion 30 thus anchors the element 10 to the wall W. Again, the disc 14 and protrusions 30 may be joined by any suitable means, such as by an adhesive or a mechanical attachment mechanism. It may also be appreciated that the disc 14 and protrusions 30 may be formed as a continuous unit. The disc 14 is also typically covered by a biocompatible polymer coating 34, such as polyurethane, polytetrafluoroethylene (PTFE), fluorinated ethylene propylene (FEP) or polyether ether ketone (PEEK). It may further be appreciated that the magnetic element 10 may have the form of a composite disc 16 such as illustrated in FIGS. 5A-5C. Or the magnetic element 10 may have any other form including cones, rods, blocks, spheres and rings, to name a few.

Figure 9A:
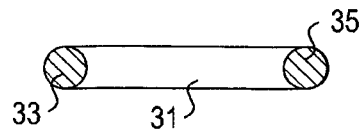
FIGS. 9A-9B illustrate magnetic elements joined by a tether.
Figure 9B:
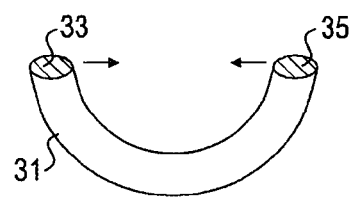
Figure 10:
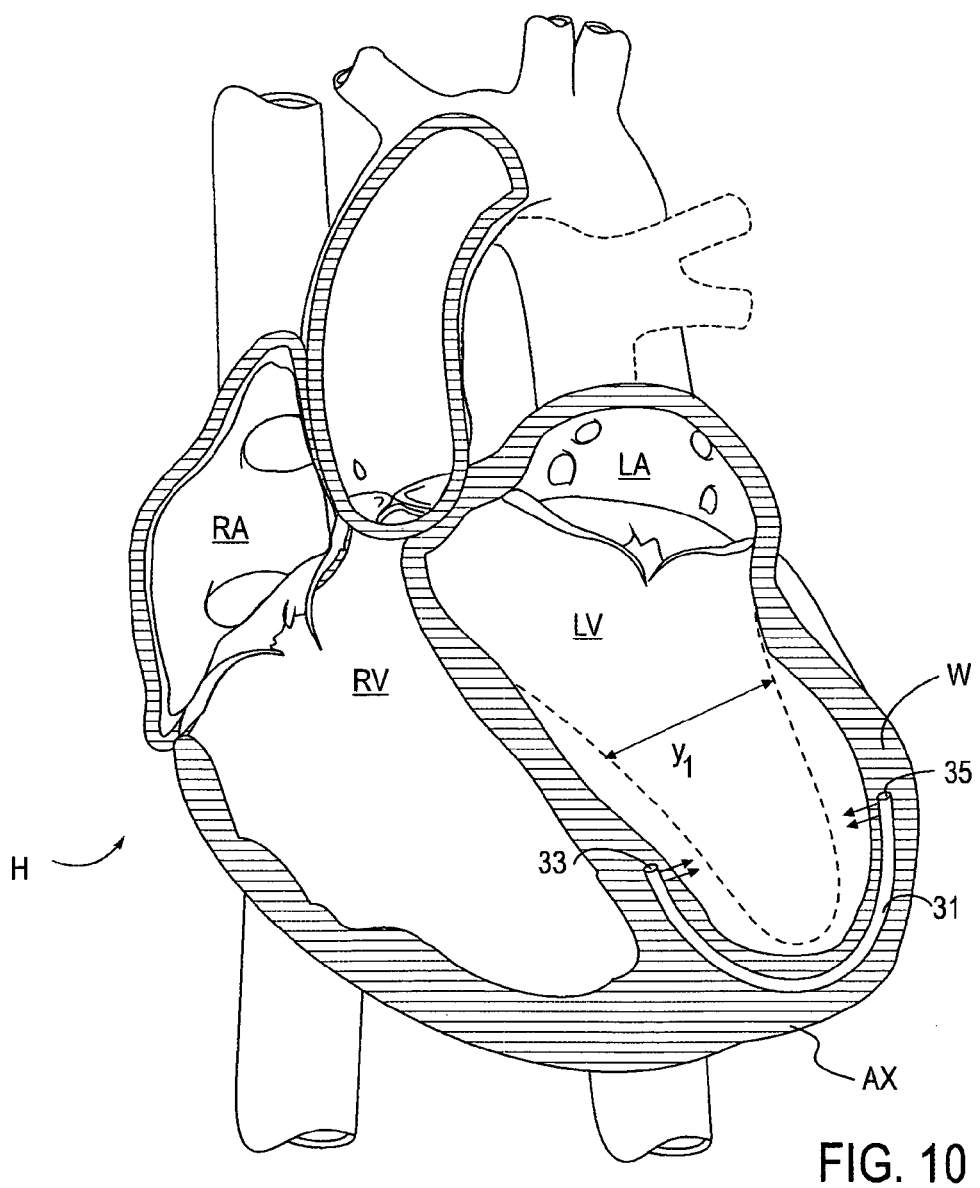
FIG. 10 illustrates the magnetic elements of FIGS. 9A-9B implanted within the wall of the left ventricle.

In still further embodiments, the magnetic elements 10 are joined by a tether 31, as illustrated in FIGS. 9A-9B. Referring to FIG. 9A, a first magnetic element 33 is connected to one end of the tether 31 and a second magnetic element 35 is connected with the other end of the tether 31. The tether 31 may be comprised of any flexible material, such as a polymer, wire, filament, thread, suture, braid, coil, or mesh, to name a few. The tether 31 may be elastic or non-elastic. Further, the tether 31 may be bioabsorbable, such as comprised of polyglycolic acid (PGA). FIG. 9A shows the tether 31 in a substantially straight configuration. Magnetic elements 33, 35 having opposite charges are magnetically attracted to each other causing the tether 31 to curve, as shown in FIG. 9B. Referring to FIG. 10, a tether 31 is shown implanted in the wall W of the left ventricle LV near the apex AX of the heart H so that magnetic elements 33, 35 are positioned on opposite sides of the left ventricle LV. Opposite charges on the first magnetic element 33 and second magnetic element 35 cause magnetic attraction. Such attraction draws the walls W of the left ventricle LV inward, toward each other, thereby reshaping the left ventricle LV. The width of the left ventricle LV is thus reduced toward the normal width $y_1$. In addition, the tether 31 pulls the wall W between the elements 33, 35 near the apex AX upward and inward as the elements 33, 35 attract. Thus, the magnetic forces are able to assist the left ventricle LV throughout the cardiac cycle, increasing the contractibility of the LV ventricle. This increases the stroke volume (SV) which increases the cardiac output (CO).

In preferred embodiments, the magnetic elements 10 are delivered to the heart wall W with the use of an endovascular delivery system. FIGS. 11A-11B illustrate an embodiment of such a delivery system 40. The system 40 includes an elongate catheter 42 having a proximal end 44 attached to a handle 45, a distal end 46, and a lumen 48 extending therethrough. In preferred embodiments, the catheter 42 has an outer diameter in the range of approximately 6-8 French. In addition, the lumen 48 may be sized for passage of a guidewire or for irrigation or contrast media injection. In some embodiments, the lumen 48 is sized for passage of a 0.081-0.035 inch guidewire; for example, the lumen 48 may have an inner diameter of approximately 0.040 inches or 1 mm. In other embodiments, the lumen 48 has an ID of 1-3 mm.

Typically, the distal end 46 includes a deflectable tip to assist in advancement of the catheter 42 through the vascular anatomy, such as from the femoral or brachial arteries. In some embodiments, the deflectable tip has a functionality similar to the deflectable tips of conventional electrophysiology or percutaneous myocardial revascularization (PMR) catheters. Advancement of the catheter 42 may be visualized with any suitable method, including fluoroscopy. Thus, in some embodiments, the catheter 42 includes a radiopaque marker 51 at the distal tip of the distal end 46. The marker 51 may be comprised of a metal such as gold or platinum. Further, the catheter 42 may be doped with radiopaque material, such as barium sulfate ($BaSO_4$).

Deflection of the catheter 42 may be achieved with the use of pullwires 43. FIG. 11B illustrates a cross-section of the catheter 42 having pullwires 43 extending through walls of the catheter 42 on opposite sides of the lumen 48. The pullwires 43 are manipulated by a deflection knob 47 on the handle 45. Manipulation of the knob 47, such as retraction of the knob 47, applies tension to one of the pullwires 43, which in turn deflects the catheter 42 toward the tensioned pullwire 43, as illustrated in FIG. 11C. FIG. 11D provides a close-up illustration of the curved distal end 46 of the catheter 42. The pullwire 43 may be locked in place, holding the catheter 42 in the deflected position, or the pullwire 43 may be released by advancement of the knob 47 back to a neutral position. Further manipulation of the knob 47, such as advancement of the knob 47, applies tension to the opposite pullwire 43, which in turn deflects the catheter 42 in the opposite direction. Again, the pullwire 43 may be locked in place or released. It may be appreciated that any number of pullwires 43 may be used. Typically, the majority of the catheter 42 is comprised of material which provides sufficient flexibility to maneuver through the vascular anatomy yet sufficient stiffness for successful advancement, such as 70A-90A to 55D-75D durometer Pebax, polyurethane or similar material. However, the distal end 46 of the catheter 42 is typically comprised of a more flexible material, such as 35A-60A durometer Pebax, polyurethane, Pellethane™ (Dow Chemical) or similar material. This difference in durometer allows deflection of the distal end 46 of the catheter 42 while maintaining relative rigidity in the remainder of the catheter 42.

Referring to FIGS. 11E-11F, the delivery system 40 includes a needle 50 having a proximal end 51 and a needle tip 52, wherein the needle 50 which extends through the lumen 48 and is extendable and retractable within the lumen 48 by a needle advancement mechanism 54. The mechanism 54 is axially fixed in relation to the handle 45 and engages the needle 52 via threads so that rotation of the mechanism 54 axially displaces the needle 50. In preferred embodiments, the needle tip 52 is advanceable beyond the distal end 46 of the catheter 42 by a stroke distance of approximately 4-10 mm. The needle 50 may be comprised of any suitable material, such as stainless steel or Nitinol®, and may have any diameter suitable for passage through the lumen 48, such as approximately 1-3 mm.

The magnetic elements 10 are loadable within the needle 50 for delivery to the heart wall W. Needle 50 has a passageway 60 extending from the proximal end 51 to the needle tip 52 so that one or more magnetic elements 10 loaded into the proximal end 51 can be advanced through the passageway 60 and expelled from the needle tip 52. The passageway 60 may have any suitable size, such as in the range of approximately 0.25-0.6 mm. In some embodiments, the passageway 60 is coated with a PTFE lining to reduce friction during advancement. Coating of the magnetic elements 10 with a biocompatible polymer, such as PTFE, also reduces friction. Referring to FIGS. 11G-11H, the elements 10 may be advanced through the passageway 60 with the use of a stylet 62. In preferred embodiments, the stylet 62 comprises an elongate shaft having a diameter sized to fit within passageway 60 and a length sized to extend from at least the distal end 51 of the needle 50 to the needle tip 52. Advancement of the stylet 62 pushes a magnetic element 10 through the passageway 60 and out of the needle tip 52, as illustrated in FIGS. 11I-11J.

In some embodiments, the delivery system 40 includes mechanisms for delivering an electrical current, such as a DC voltage or radiofrequency, directly to the magnetic elements 10. In the case of DC voltage, the electrical current may be supplied with the use of DC batteries. Such application of current may be used to bend protrusions of the magnetic elements 10, as described above, to assist in anchoring the elements 50 in the heart wall W.

Figure 12:
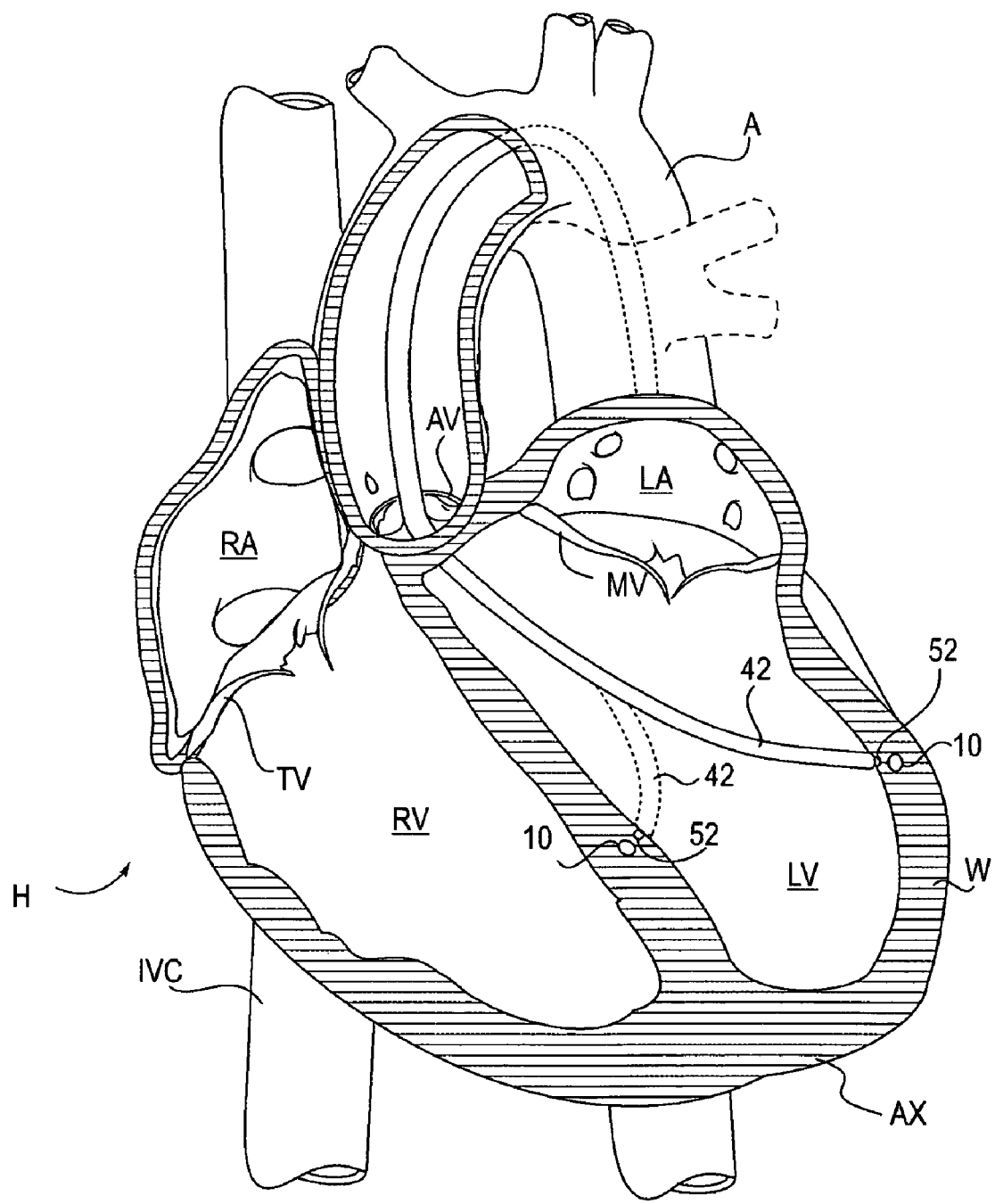
FIG. 12 illustrates an approach for endovascular delivery of magnetic elements to the walls of the left ventricle.

FIG. 12 illustrates one approach for endovascular delivery of magnetic elements 10 to the walls W of the left ventricle LV. Here, a femoral approach is shown wherein the delivery catheter 42 is advanced through the aorta A and the aortic valve AV. Typically, the catheter 42 is advanced through a sheath, such as a 9-10 French sheath, positioned within the femoral artery (not shown). Under fluoroscopy or other methods of guidance, the distal end 46 of the catheter 42 is guided within the left ventricle LV and positioned near or against the ventricular wall W at a target location. After verification of the appropriate positioning of the catheter 42, the needle tip 52 is advanced into the wall W at the target location, as illustrated in FIG. 12. One or more magnetic elements 10 are then advanced through the needle and out of the needle tip 52 so that the element(s) 10 are positioned within the wall W. The catheter 42 may then be repositioned so that the distal end 46 is disposed near or against the ventricular W at another target location, as indicated by dashed image of the catheter. Thus, one or more magnetic elements 10 may be positioned at other target locations around the left ventricle LV. This may be repeated any number of times.

It may be appreciated that the left ventricle LV may alternatively be approached by advancement of the catheter 42 through the inferior vena cava IVC, into the right atrium RA, across the interatrial septum, into the left atrium LA and through the mitral valve MV. Similarly, the right ventricle RV may be approached through the inferior vena cava IVC, into the right atrium RA and through the tricuspid valve TV. A variety of other endovascular approaches may also be used. It may also be appreciated that non-endovascular approaches may also be used wherein the magnetic elements 10 are placed on or within the walls W by open chest surgery or through minimally invasive procedures where access is achieved thoracoscopically.

Figure 13:
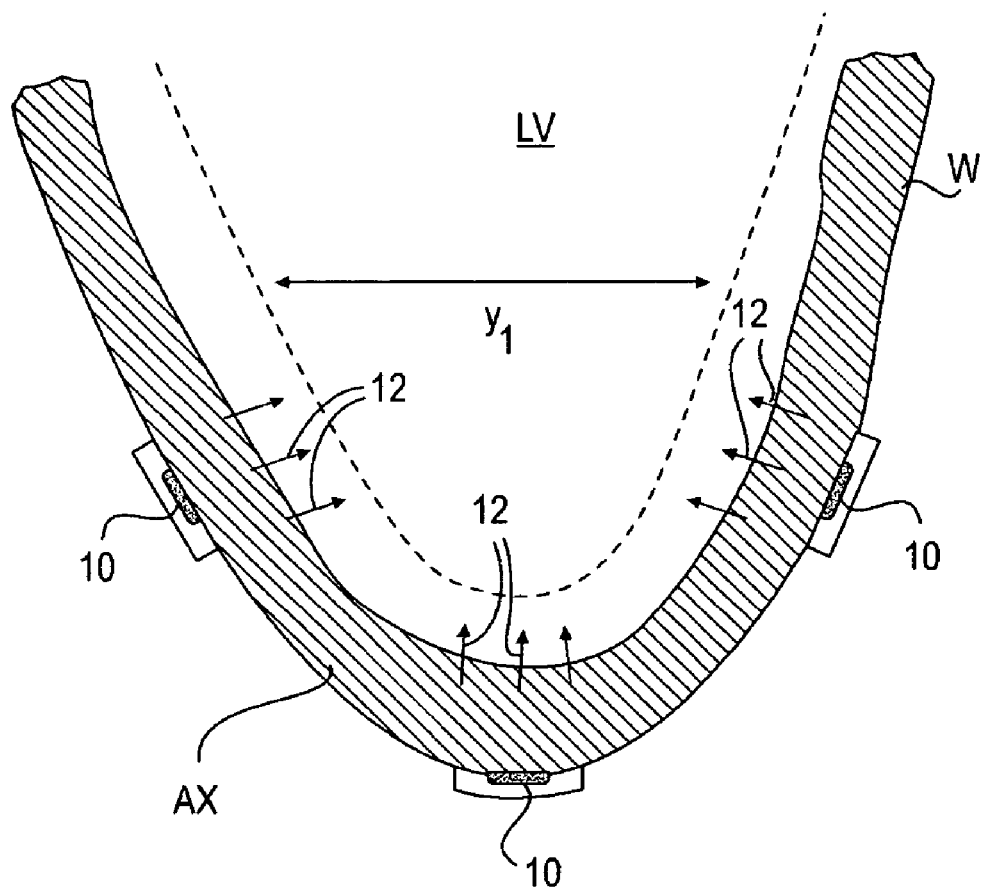
FIG. 13 illustrates magnetic elements implanted on an external surface of the left ventricle.

Alternatively or in addition, magnetic elements 10 may be positioned on an external surface of the heart. In preferred embodiments, the elements 10 are positioned on the external surfaces of the walls of the ventricles. For example, as illustrated in FIG. 13, magnetic elements 10 may be implanted on the surface of the left ventricle LV near the apex AX of the heart. The magnetic elements 10 have opposing poles so that the magnetic elements 10 attract each other, as indicated by arrows 12. Such attraction draws the walls W of the ventricle LV inward, toward each other, thereby reshaping the ventricle LV. The width of the left ventricle LV is thus reduced toward normal width $y_1$. The magnetic forces are able to assist the left ventricle LV throughout the cardiac cycle, increasing the contractibility of the left ventricle LV. This increases the stroke volume (SV) which increases the cardiac output (CO). It may be appreciated that the magnetic elements 10 may interact with elements 10 positioned within the ventricular walls and/or within the ventricles to further assist in reshaping the ventricles.

Externally placed magnetic elements 10 may have any of the forms described and illustrated above and may optionally include a patch to assist in attaching the element 10 to the heart wall W. FIGS. 14A-14B illustrate an embodiment of a magnetic element 10 including a magnetic core 70 attached to a patch 72. In this embodiment, the core 70 is in the shape of a disc having a diameter in the range of approximately 0.1-3 mm and a thickness of 0.1-3 mm. It may be appreciated that the magnetic core 70 may have any suitable size and shape, including discs, cones, rods, blocks, spheres, and rings to name a few. The magnetic core 70 is comprised of any suitable magnetic material, such as Neudynium Iron Boron (Nd Fe B), Samarium Cobalt (Sm Co) or Aluminum Nickel Cobalt (Al Ni Co). Such a magnetic core 70 can provide a static magnetic field of approximately 300 Gauss.

In this embodiment illustrated in FIG. 14A, the magnetic core 70 is disposed in the center of the patch 72. The patch 72 may be comprised of any material which provides suitable flexibility and mating with the surface of the heart, such as Dacron®. In this embodiment, the patch 72 has a circular shape with a diameter in the range of approximately 0.120-0.500 inches and a thickness in the range of approximately 0.005-0.050 inches. The patch 72 may also include suture holes 74 to assist in suturing the patch to the heart wall. In preferred embodiments, the patch 72 includes 6-12 suture holes 74 located around the peripheral edge of the patch 72. Each suture hole 74 may have a diameter of 0.010±0.005 inches. FIG. 14B provides a cross-sectional view of the magnetic element 10 of FIG. 14A.

FIGS. 15A-15B illustrate a similar embodiment wherein the magnetic element 10 includes two magnetic cores 70a, 70b disposed on the patch 72. Here, the magnetic cores 70a, 70b have opposite charges. It may be appreciated that any number of magnetic cores may be disposed on the patch 72, and the magnetic cores may have any charge and may be in any arrangement.

FIGS. 16A-16B illustrate another embodiment of a magnetic element 10 including a magnetic core 80 attached to a patch 82. In this embodiment, the core 80 is in the shape of a disc having a diameter in the range of approximately 0.040-0.120 inches and a thickness of 0.010-0.120 inches. It may be appreciated that the magnetic core 80 may have any suitable size and shape, including discs, cones, rods, blocks, spheres, and rings to name a few. The magnetic core 80 is comprised of any suitable magnetic material, such as Neudynium Iron Boron (Nd Fe B), Samarium Cobalt (Sm Co) or Aluminum Nickel Cobalt (Al Ni Co).

In this embodiment illustrated in FIG. 16A, the magnetic core 80 is disposed in the center of the patch 82. The patch 82 may be comprised of any material which provides suitable flexibility and mating with the surface of the heart, such as Dacron®. In this embodiment, the patch 82 has a circular shape with a diameter in the range of approximately 0.120-0.500 inches and a thickness of approximately 0.040±0.005 inches. FIG. 16B provides a cross-sectional view of the magnetic element 10 of FIG. 16A.

The magnetic elements 10 are attached to the external surface of the heart by open heart surgical methods or minimally invasive thoracoscopic methods. The patches are typically sewn to the heart with the use of sutures. Alternatively or in addition, the patches may be glued to the heart with a tissue adhesive. As mentioned above, the magnetic forces are able to assist the ventricles throughout the cardiac cycle, increasing the contractibility of the ventricles. This increases the stroke volume (SV) which increases the cardiac output (CO).

Figure 17A:
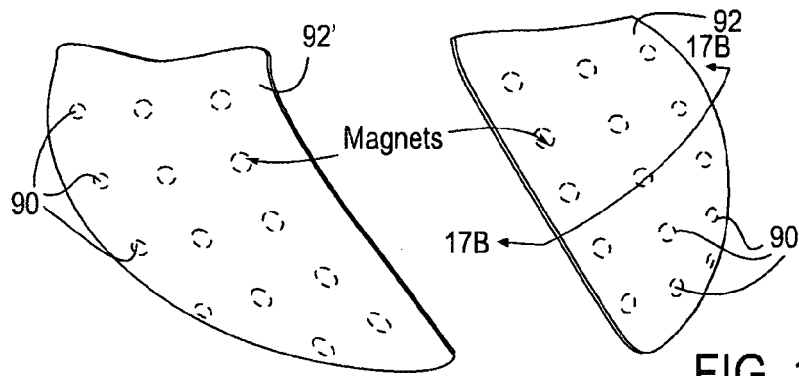
FIGS. 17A-17C illustrate an embodiment of a magnetic element which includes a plurality of magnetic cores disposed on a larger patch.
Figure 17B:
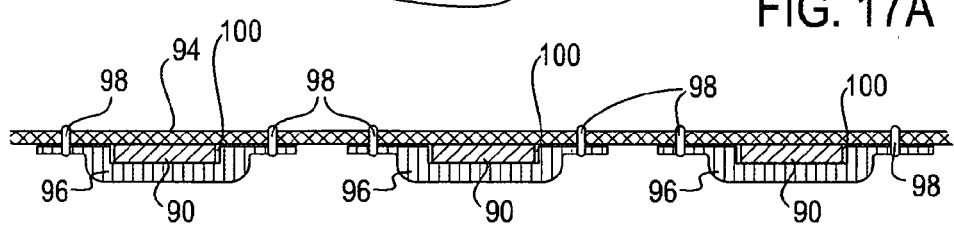
Figure 17C:
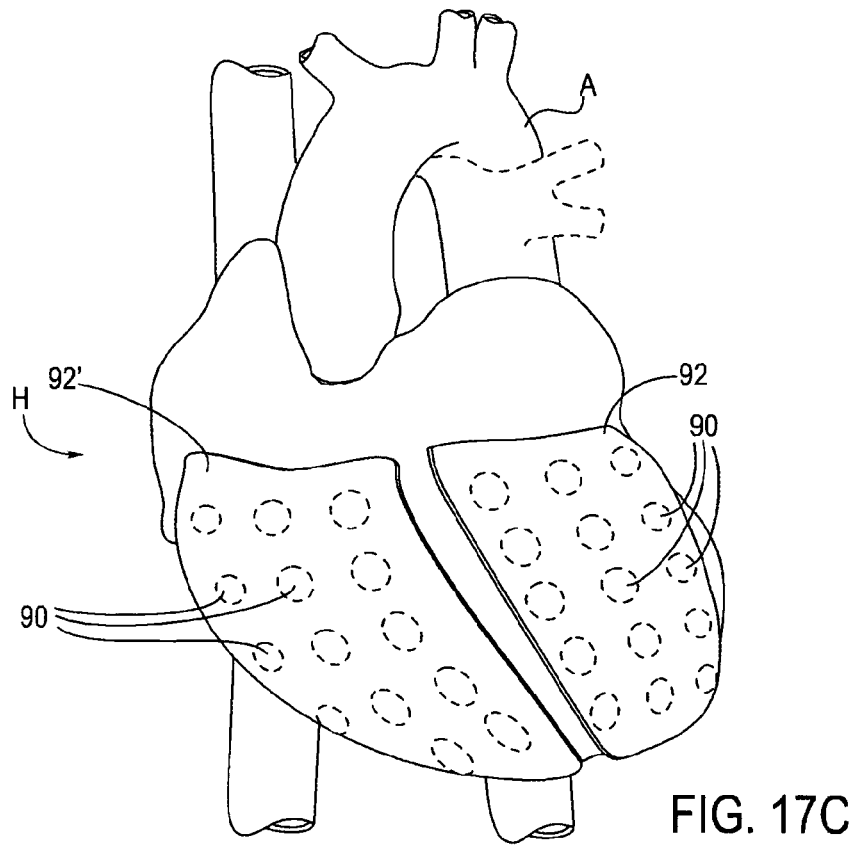

FIGS. 17A-17C illustrate yet another similar embodiment wherein the magnetic element 10 includes a plurality of magnetic cores 90 disposed on a larger patch 92. In this embodiment, the cores 90 are in the shape of individual discs having diameters in the range of approximately 0.040-0.120 inches and thicknesses of 0.010-0.120 inches. It may be appreciated that the magnetic cores 90 may have any suitable size and shape, including discs, cones, rods, blocks, spheres, and rings to name a few. The magnetic cores 90 are comprised of any suitable magnetic material, such as Neudynium Iron Boron (Nd Fe B), Samarium Cobalt (Sm Co) or Aluminum Nickel Cobalt (Al Ni Co). The larger patch 92 may be comprised of any material which provides suitable flexibility and mating with the surface of the heart, such as Dacron®.

The larger patch 92 is sized and shaped to cover a more extensive portion of the surface of the heart, such as a surface covering an atrium or ventricle. FIG. 17A illustrates two such patches 92, 92', a left ventricle patch 92 and a right ventricle patch 92'. It may be appreciated that any number of magnetic cores 90 may be disposed on the patches 92, 92', and the magnetic cores 90 may have any charge and may be in any arrangement. The cores 90 may also be attached to the patches 92, 92' by any suitable means, such as by suturing, adhering with adhesive, or confining in a pocket. FIG. 17B illustrates a cross-sectional view of patch 92. As shown, the patch 92 is comprised of a first layer of material 94 and a second layer of material 96, wherein the magnetic cores 90 are captured between the layers 94, 96. The layers 94, 96 may be sutured 98 or sewn together creating pockets 100 within which the cores 90 reside.

The magnetic elements 10 are attached to the external surface of the heart, as illustrated in FIG. 17C, by open heart surgical methods or minimally invasive thoracoscopic methods. The patches 92, 92' are typically sewn to the heart with the use of sutures. Alternatively or in addition, the patches may be glued to the heart with a tissue adhesive. In some embodiments, the cores 90 on the left ventricle patch 92 are positively charged and the cores on the right ventricle patch 92' are negatively charged. Thus, the oppositely charged patches 92, 92' apply force to opposite sides of the heart, compressing the ventricles therebetween. The magnetic forces are able to assist the ventricles throughout the cardiac cycle, increasing the contractibility of the ventricles. This increases the stroke volume (SV) which increases the cardiac output (CO).

Figure 18A:
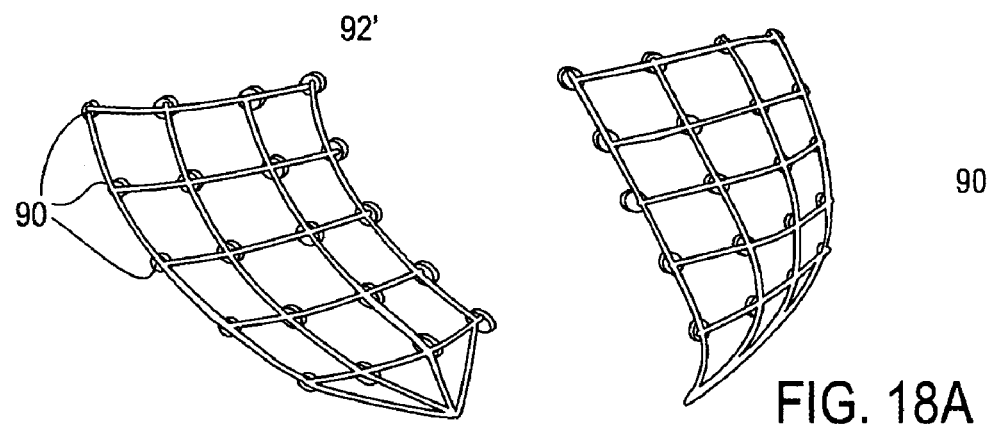
FIGS. 18A-18B illustrate an embodiment of a magnetic element wherein each of the patches are comprised of a net.
Figure 18B:
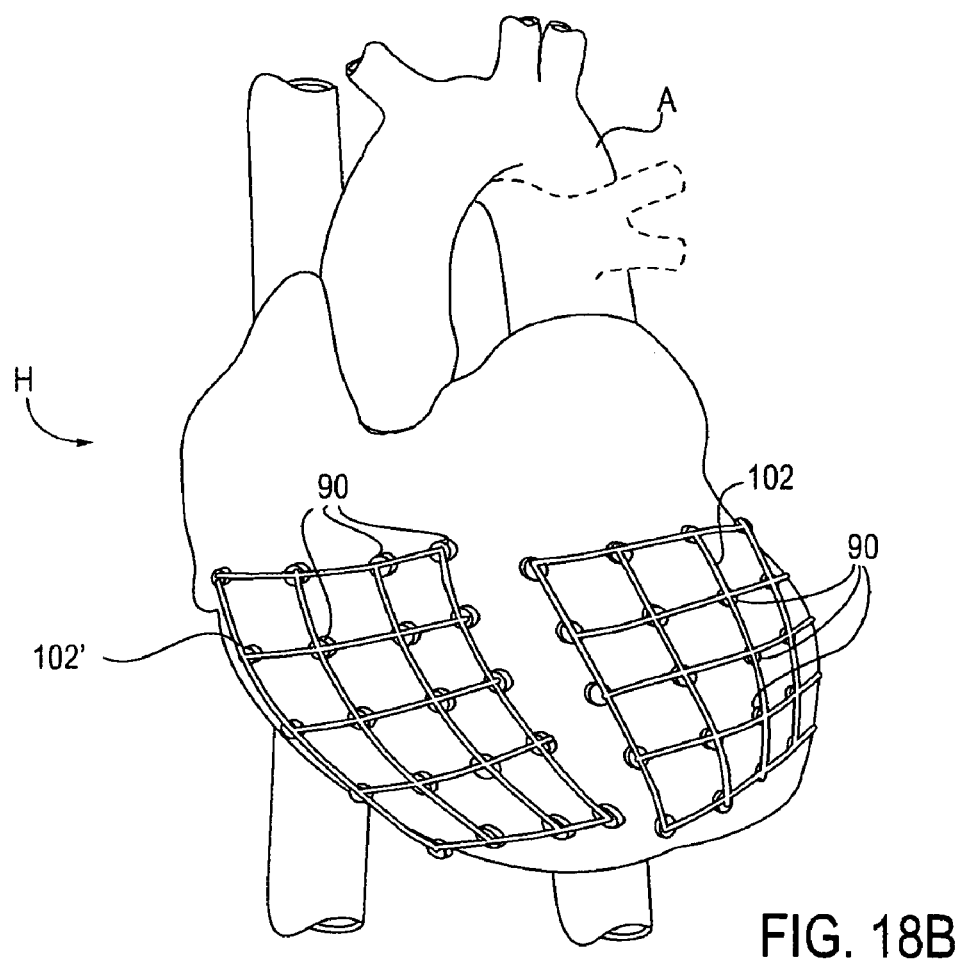

FIGS. 18A-18B illustrate another embodiment wherein each of the patches are comprised of a net 102, 102' respectively. The nets 102, 102' have the form of an openwork mesh made of strands that are woven or knotted together at regular or irregular intervals. The strands may be comprised of suture, threads, filaments, wires or other suitable materials and may be elastic or non-elastic. The magnetic cores 90 typically have the same features as described above. The cores 90 may also be attached to the nets 102, 102' by any suitable means, such as by suturing or adhering with adhesive. The cores 90 may be attached at any locations and in any arrangement on the nets 102, 102'. The nets 102, 102' are sized and shaped to cover a desired portion of the surface of the heart, such as a surface covering an atrium or ventricle. The magnetic elements 10 are attached to the external surface of the heart, as illustrated in FIG. 18B, by open heart surgical methods or minimally invasive thoracoscopic methods. The nets 102, 102' are typically sewn to the heart with the use of sutures and/or glued to the heart with a tissue adhesive. Again, in some embodiments, the cores 90 on a left ventricle net 102 are positively charged and the cores on the right ventricle net '102 are negatively charged. Thus, the oppositely charged nets 102, 102' apply force to opposite sides of the heart, compressing the ventricles therebetween. The magnetic forces are able to assist the ventricles throughout the cardiac cycle, increasing the contractibility of the ventricles. This increases the stroke volume (SV) which increases the cardiac output (CO).

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A method for treating cardiomyopathy, comprising:
   implanting a first magnetic element having a first charge at least partially within a first tissue area of the heart anatomy, wherein the first magnetic element includes at least one protrusion including a screw shape, and wherein implanting the first magnetic element comprises advancing at least a portion of the at least one protrusion by rotating the screw shape at least partially within the first tissue area of the heart anatomy; and
   implanting a second magnetic element having a second charge at least partially within a second tissue area of the heart anatomy, wherein the first and second magnetic elements are arranged so as to magnetically attract each other during diastole and systole causing at least one of the first or second tissue areas to move in a manner which contracts the heart anatomy throughout the cardiac cycle,
   wherein at least one of the first tissue area or the second tissue area comprises a wall of a ventricle and contracting the heart anatomy comprises increasing the contractibility of the ventricle.

2. The method of claim 1, further comprising:
   implanting a third magnetic element having a third charge at least partially within a third tissue area of the heart anatomy, wherein the third magnetic element is positioned so as to magnetically interact with either or both the first and second magnetic element causing at least one of the first, second or third tissues areas to move in a manner which reshapes the heart anatomy.

3. The method of claim 1, wherein increasing the contractibility of the ventricle comprises drawing at least one wall of the ventricle inward reducing a width of the ventricle.

4. The method of claim 1, wherein at least one of the first tissue area or the second tissue area comprises a wall of a septum.

5. The method of claim 1, wherein at least one of the first tissue area or the second tissue area comprises a wall of an atrium.

6. A method for reshaping the left ventricular of a heart of a patient, comprising:
   implanting a first magnetic element having a first charge at least partially within a first tissue area of the left ventricle of the patient's heart; and
   implanting a second magnetic element having a second charge at least partially within a second tissue area of the left ventricle of the patient's heart, wherein the first and second magnetic elements are arranged so as to magnetically attract each other during diastole and systole of the patient's heart causing at least one of the first or second tissue areas to move in a manner which increases the contractibility of the left ventricle of the patient's heart throughout the cardiac cycle.

7. A method of reshaping heart anatomy, comprising:
   attaching a first magnetic element having a first charge to a first target location on a surface of the heart anatomy; and
   attaching a second magnetic element having a second charge to a second target location on the surface of the heart anatomy, wherein both of the first target location and the second target location are on a wall of a ventricle, wherein the first and second magnetic elements are arranged so as to magnetically attract each other during diastole and systole causing the first and second target locations to move in a manner which increases the contractibility of the ventricle throughout the cardiac cycle.

* * * * *